United States Patent

Kreidl et al.

[11] Patent Number: 5,122,607
[45] Date of Patent: Jun. 16, 1992

[54] RACEMIC AND OPTICALLY ACTIVE OCTAHYDRO-INDOLO(2,3-A) TETRAHYDROPYRANYL (2,3-C) QUINOLIZINE DIESTER DERIVATIVES AND PROCESS FOR PREPARING THE SAME

[75] Inventors: János Kreidl; Csaba Szántay; Lajos Szahó; Mária Farkas née Kirják; György Kalaus; Katalin Nógrádi; András Nemes; Judit Mészáros née Brill; Zsuzsanna Aracs née Tischler; Béla Stefkó; János Sápi; Ida Deutsch née Juhász; István Hegedüs; Béla Benke; Kálmán Gráf; Kálmám Gáf; Katalin Horváth née Berki, all of Budapest, Hungary

[73] Assignee: Richter Gedeon Vegyesczeti Gyar RT., Budapest, Hungary

[21] Appl. No.: 542,485

[22] Filed: Jun. 21, 1990

[30] Foreign Application Priority Data

Jun. 21, 1989 [HU] Hungary ............... 3163/89
Jun. 21, 1989 [HU] Hungary ............... 3165/89

[51] Int. Cl.⁵ .................. C07D 455/00; C07D 461/00
[52] U.S. Cl. ......................... 546/48; 546/70; 546/51
[58] Field of Search ................... 546/48, 70

[56] References Cited

U.S. PATENT DOCUMENTS

| | | | |
|---|---|---|---|
| 4,138,489 | 2/1979 | Thal et al. ............ | 546/70 X |
| 4,345,082 | 8/1982 | Szántay et al. ............ | 546/51 |
| 4,456,607 | 6/1984 | Szántay et al. ............ | 546/70 X |
| 4,464,534 | 8/1984 | Szántay et al. ............ | 546/51 |
| 4,464,535 | 8/1984 | Szántay et al. ............ | 546/51 |
| 4,474,960 | 10/1984 | Szántay et al. ............ | 546/70 |

FOREIGN PATENT DOCUMENTS 0050492 4/1982 European Pat. Off. ............ 546/70

Primary Examiner—Diana G. Rivers
Attorney, Agent, or Firm—Herbert Dubno; Jonathan Myers

[57] ABSTRACT

New intermediate compounds are disclosed of the formula I,

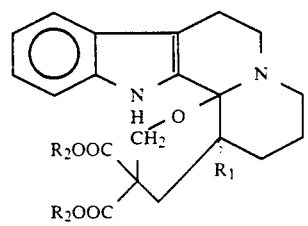

Ia wherein
  $R_1$ and $R_2$ are independently alkyl having 1 to 4 carbon atoms,
or acid-addition salts thereof of formula Ib,

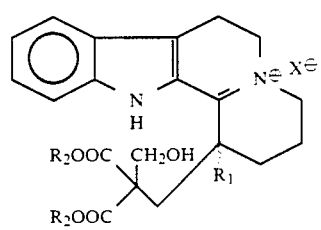

Ib wherein X represents an acid residue.

and a process for the preparation of the intermediate compounds.

9 Claims, No Drawings

RACEMIC AND OPTICALLY ACTIVE OCTAHYDRO-INDOLO(2,3-A) TETRAHYDROPYRANYL (2,3-C) QUINOLIZINE DIESTER DERIVATIVES AND PROCESS FOR PREPARING THE SAME

FIELD OF THE INVENTION

The present invention relates to novel racemic and optically active octahydro-indolo 2,3-a tetrahydropyranyl [2,3-c] quinolizine diester derivatives of formula Ia

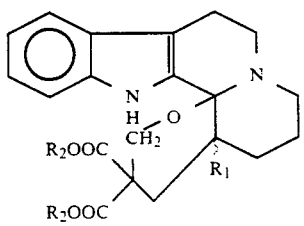

wherein
$R_1$ and $R_2$ are independently alkyl having 1 to 4 carbon atoms,
and to the acid addition salts thereof represented by formula Ib

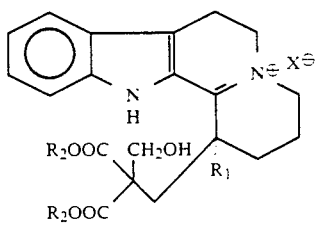

wherein $R_1$ and $R_2$ are the same as defined hereinabove and X represents an acid residue.

The present invention also covers a process for the preparation of the compounds of formulae Ia and Ib.

The racemic or optically active compounds of formulae Ia and Ib are very important intermediates for the synthesis of pharmaceutically active compounds of eburnane skeleton, such as vincamine, vincamone and the apovincaminic acid esters, e.g. Cavinton.

From the novel compounds of the present invention the novel octahydro-indolo[2,3-a] quinolizine diester derivatives can be prepared according to the method described in or simultaneously filed application and in present example 11, and and from these compounds the known hydroxyimino-octahydro-indolo [2,3-a] quinolizine derivatives can be prepared according to Example 12. From these hydroxyimino derivatives the pharmaceutically active compounds of eburnane skeleton can be prepared in one step according to the process described in Example 13 or 14.

SUMMARY OF THE INVENTION

The racemic or optically active compounds of formulae Ia and Ib are prepared by reacting a hexahydro-indolo[2,3-a] quinolizine diester derivative of formula II,

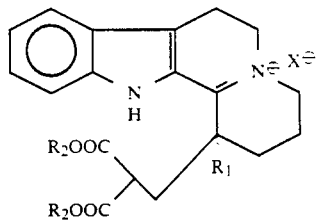

wherein $R_1$, $R_2$ and X are the same as defined hereinabove, with formaldehyde in an inert organic solvent in the presence of a base and if desired resolving the racemic compounds of formula Ia thus obtained and/or transforming them into acid-addition salts of formula Ib.

In the above formulae $R_1$ and $R_2$ stand for alkyl having 1 to 4 carbon atoms, which alkyl moiety can be straight or branched, e.g. methyl, ethyl, n-propyl, i-propyl, n-butyl, i-butyl or t-butyl.

As an example of the acid residue represented by X, the residues of organic or inorganic acids which are inert in the reaction, such as perchlorate, tartarate, oxalate or dibenzoyl tartarate can be mentioned.

The hexahydro-indolo 2,3-a quinolizinium ester derivatives of formula II, used as starting materials, can be prepared according to the method described in British patent specification No. 2,051,794.

In the process of the present invention the starting materials of formula II are reacted with formaldehyde in the presence of at least equimolar amount of a base in an inert organic protic or aprotic solvent, e.g. in ethanol or acetone. Preferably a protic solvent is used. The aqueous mixture of the above solvents can also be used. As a base e.g. sodium carbonate, an alkali metal alcoholate or alkyl amine, preferably triethyl amine, is used.

The compounds of formula II used as starting materials can be such quinolizinium ester derivatives wherein X represents an acid residue referred to hereinabove.

The reaction is carried out under atmospheric pressure at a temperature of 20° to 60° C.; the reaction time is 2 to 5 hours.

The racemic compounds of formula Ia can be obtained in very good yields. They can be recovered from the reaction mixture in a very simple way by e.g. precipitation or by adding a solvent to the reaction mixture which reduces their solubility. The crystalline substance thus obtained is separated by filtration. It is especially preferred if the reaction is carried out in a protic solvent, e.g. in ethanol, as the product thus obtained directly separates from the reaction mixture and it can be recovered by filtration.

The racemic compounds of formula Ia thus obtained can be transformed into their acid-addition salts of formula Ib in a manner known per se, e.g. by treating with an acid. For this purpose an organic or inorganic acid which is chemically inert towards the compound of formula Ia, e.g. hydrogen halides, perhalogenic acid, oxalic acid, tartaric acid or tartaric acid derivatives, etc. can be used.

The racemic compounds of formula Ia obtained after the reaction with formaldehyde can be resolved in a resolution method known per se. As resolution agent a commonly used optically active acid or acidic compound, e.g. tartaric acid, dibenzoyl tartaric acid, camphorsulfonic acid, di-p-toluene-tartaric acid, dibenzoyl tartaric acid monodimethyl amide, etc. can be used. Tartaric acid and dibenzoyl tartaric acid are preferred.

The resolution can be carried out in a suitable inert organic solvent, e.g. in a protic organic solvent such as alkanols having 1 to 4 carbon atoms (ethanol, methanol, etc.) or chlorinated hydrocarbons, preferably aliphatic chlorinated hydrocarbons (dichloromethane, dichloroethane etc.) or in a mixture thereof. A dipolar aprotic solvent, e.g. a ketone, preferably acetone, can also be used. The resolution is carried out under atmospheric pressure at a temperature between 0° C. and the boiling point of the solvent used, preferably at a temperature of 20° to 50° C.

In the course of our experiments surprisingly we have found that if special resolution agents, e.g. dibenzoyl tartaric acid is used, the resolution can completely be carried out by using only half the amount of the commonly used resolving agent, i.e. by using only 0.5 molar equivalent of resolving agent calculated for the racemic compound. Then after the separation of the insoluble acid-addition salt formed with the resolution agent the other antipode remains in the solution in the form of a base. This finding is very importance when the process is carried out on an industrial scale; significant amounts of resolving agent can be spared.

The novel optically active compounds of the formula Ia, wherein the 1-alkyl group is in alpha or in beta position, can be recovered from the acid-addition salt thereof of formula Ib, formed with the resolving agent, wherein X represents an acid residue corresponding to the resolving acid, in a manner known per se by liberating the base by the addition of at least an equimolar amount of a base to the salt.

If desired, the optically active compounds of formula Ia can be transformed into acid-addition salts of formula Ib, wherein X represents any acid residue listed hereinabove, in a manner known per se.

According to a preferred embodiment of the present invention the resolution is carried out with the aid of an optically active acidic resolution agent, e.g. with (−)-dibenzoyl tartaric acid. Carrying out the resolution with a molar equivalent of resolving agent, the (−)-diastereomeric salt of formula Ib, wherein the 1-alkyl group is in the beta-position, precipitates and it can be separated by filtration. The (+)-diastereomeric salt of formula Ib, wherein the 1-alkyl group is in alpha-position, remains in the solution and the corresponding compound of formula Ia can be liberated in a manner known per se and isolated by evaporation.

According to an other embodiment of the process of the invention, the dissolved base can be precipitated by the addition of a solvent which is not soluble in the solvent used for the resolution, and the product can be filtered off.

If desired, the base of formula Ia can be transformed into an acid-addition salt thereof in a manner known per se.

This antipode of formula Ia carrying the 1-alkyl group in the alpha-position or the acid-addition salt thereof of formula Ib can be used for the synthesis of pharmaceutically active eburnane-derivatives. If desired, the solution comprising the salt of formula Ib can also be used for the synthesis of pharmaceutically active compounds.

If desired, the base of formula I can be liberated from the other diastereomeric salt of formula Ib, carrying the 1-alkyl group in beta-position, separated during the resolution.

The resolution can also be carried out with the aid of (+)-dibenzoyl tartaric acid. In this case the diastereomeric salt carrying the 1-alkyl group in the alpha-position separates and the compound carrying the 1-alkyl group in the beta-position remains in the solution.

According to an other preferred embodiment of the process of the invention, the resolution is carried out with the aid of 0.5 molar equivalent of optically active acidic resolving agent, e.g. with (−)-dibenzoyl tartaric acid, calculated for the racemic compound. The separated salt of formula Ib formed with the resolving acid, carrying the 1-alkyl group in the beta-position, is recovered. Then the solution comprises only the base of formula Ia, carrying the 1-alkyl group in the alpha-position. This base can be isolated according to the above-mentioned methods or transformed into an acid-addition salt of formula Ib, or if desired, used in the next reaction step without isolation.

The invention is further illustrated by the following non-limiting examples.

EXAMPLE 1

(±)-14,14-bis(ethoxycarbonyl)-1-ethyl-1,2,3,4,6,7,12,12b-octahydro-indolo[2,3-a] tetrahydropyranyl 2,3-quinolizine (Ia; $R_1$, $R_2$=ethyl)

55.3 g (0.12 mole) of (±)-1-ethyl-1-(2',2'-diethoxycarbonyl-ethyl)-1,2,3,4,6,7-hexahydro-12H-indolo [2,3-c] quinolizine-5-ium hydrochloride are suspended in 160 ml of ethanol, then 4.8 g (0.16 mole) of paraformaldehyde and 20.0 ml (0.14 mole) of triethyl amine are added and the reaction mixture is stirred at a temperature of 50° C. for 2 hours. Then the mixture is cooled to a temperature of 0° C. The crystalline suspension is filtered off and washed with cold alcohol. Thus 50.7 g (93%) of the desired compound are obtained.

Melting point: 153°–154° C.

UV (EtOH, $\lambda_{max}$): 296 nm.

EXAMPLE 2

14,14-bis(methoxycarbonyl)1-ethyl-1,2,3,4,6,7,12,12b-octahydro-indolo[2,3-a] tetrahydropyranyl[2,3c] quinolizine (Ia; $R_1$=ethyl, $R_2$=methyl)

13.0 g (0.03 mole) of (±)-1-ethyl-1-(2',2'-dimethoxycarbonyl-ethyl)-1,2,3,4,6,7-hexahydro-12H-indolo [2,3-a] quinolizine-5-ium hydrochloride are suspended in 30 ml of isopropanol, then 1.2 g (0.04 mole) of paraformaldehyde and 4.5 ml (0.033 mole) of triethyl amine are added and the reaction mixture is stirred at a temperature of 50° C. for 2 hours. The mixture is cooled to a temperature of 0° C. and stirring is continued for another 2 hours. Thus 11 6 g (91%) of the desired compound are isolated.

Melting point: 139°–142° C.

IR (KBr): 3450 (indole NH), 1755, 1720 cm$^{-1}$ (CO), 1270 cm$^{-1}$ (C—O—C)

UV (296 nm $\lambda_{max}$) (EtOH, HCl salt): 362 nm

MS (M/e, %): 426 (M$^+$, 24), 397 (8), 367 (8), 282 (15), 265 (30), 252 (45), 237 (100), 113 (62).

EXAMPLE 3

14,14-bis(ethoxycarbonyl)-1-ethyl-1,2,3,4,6,7,12,12b-octahydro-indolo[2,3-a] tetrahydropyranyl[2,3-c] quinolizine (Ia; $R_1$, $R_2$=ethyl)

39.10 g (0.05 mole) of (±)-1-ethyl-1-(2',2'-diethoxycarbonyl-ethyl)-1,2,3,4,6,7-hexahydro-12H-indolo [2,3-a] quinolizine-5-ium hydrochloride are suspended in 60 ml of ethanol, then 1.8 g (0.06 mole) of paraformaldehyde and 7.48 g (0.11 mole) of sodium ethylate are added and the reaction mixture is stirred at room temperature for 3 hours. Then the mixture is cooled to a temperature of 10° C. and 50 ml of water are added dropwise. The crystalline suspension is filtered off and washed with 2×20 ml of water, finally covered with ethanol. The 20.2 g (89%) of the desired compound are obtained.

EXAMPLE 4

1-Ethyl-1-(2'-dicarbethoxy-2'-hydroxymethyl-ethyl)-1-ethyl-1,2,3,4,6,7-hexahydro-indolo[2,3-a] quinolizine chloride (compound of formula Ib)

47.0 g (0.06 mole) of 1-ethyl-1-(2'-diethoxycarbonyl)-1,2,3,4,6,7-hexahydro-12H-indolo [2,3-a] quinolizine-5-ium-d-tartarate are suspended in 120 ml of ethanol, then 1.98 g (0.066 mole) of paraformaldehyde and 6.36 g (0.06 mole) of sodium carbonate dissolved in 120 ml of water are added and the reaction mixture is vigorously stirred at a temperature of 30° C. for 2 hours. Then the mixture is cooled to a temperature of 10° C. The crystalline suspension is filtered off and washed twice with 40 ml of water each. The product is suspended in a mixture of 40 ml of ethanol and 40 ml of ethyl acetate, then the pH of the mixture is adjusted to 4 by adding hydrochloric alcohol. Thereafter the mixture is cooled to a temperature of 0° C. filtered off and dried. Thus 36.7 g (75%) of the desired compound are obtained.

Mp: 123°–125° C.
UV (EtOH, $\lambda_{max}$)≦362 nm

EXAMPLE 5

Resolution of
(±)-14,14-bis(ethoxycarbonyl)-1-ethyl-1,2,3,4,6,7,12,12b-octahydro-indolo[2,3-a] tetrahydropyranyl[2,3-c] quinolizine (compound of formula Ia)

To 7.28 g (16 millimoles) of racemic 14,14-bis(ethoxycarbonyl)-1-ethyl-1,2,3,4,6,7,12,12b-octahydro-indolo [2,3,-a] tetrahydropyranyl[2,3-c] quinolizine 40.0 ml of acetone are added, then 3.3 g (8.8 millimoles) of (−)-dibenzoyl-d-tartaric acid monohydrate are added to the reaction mixture. The reaction mixture is stirred at room temperature for an hour, then cooled to 10° C. the precipitated crystals are filtered off, washed with acetone and dried. Thus 6.6 g (8.16 millimoles) of (−)-1α-(2'-dicarbethoxy-2'-hydroxymethyl-ethyl)-1β-ethyl-1,2,3,4,6,7-hexahydro-indolo [2,3-a] quinolizium-dibenzoyl tartarate are obtained. The base content of the product is 55.8% according to perchloric acid titration.

$[\alpha]^{20}_D = -72.5°$ (c = 1, dimethyl formamide)
Melting point: 140°–142° C. (decomposition)
Yield: 51.0%

Then 3 ml of 5% sodium carbonate solution are added to the filtrate and 50 ml of water are added at a temperature of 20° C. to 25° C. The solution is cooled to 0° C., washed with 5% acetonic water and dried.

Thus 3.5 g (7.68 millimoles) of (+)-14,14-bis(ethoxycarbonyl)-1α-ethyl-1,2,3,4,6,7,12,12b-octahydro-indolo[2,3-a] tetrahydropyranyl[2,3-c] quinolizine are obtained.

Active ingredient content (on the basis of titration with perchloric acid): 99.8%.

$[\alpha]^{20}_D = +95.7°$ (c = 1, dichloromethane)

Melting point: 134°–137° C. (decomposition). Yield: 48.0%.

EXAMPLE 6

Resolution of
(±)-14,14-bis(ethoxycarbonyl)-1-ethyl-1,2,3,4,6,7,12,12b-octahydro-indolo[2,3-a] tetrahydropyranyl[2,3-c] quinolizine (compound of formula Ia)

To 7.28 g (16 millimoles) of racemic 14,14-bis(ethoxycarbonyl)-1-ethyl-1,2,3,4,6,7,12,12b-octahydro-indolo [2,3-a] tetrahydropyranyl[2,3-c] quinolizine 70.0 ml of acetone are added, then 6.0 g (16 millimoles) of (−)-dibenzoyl-d-tartaric acid monohydrate are added to the reaction mixture. The reaction mixture is stirred at room temperature for an hour, then filtered off, washed with acetone and dried. Thus 6.76 g (8.32 millimoles) of (−)-1α-(2'-dicarbethoxy-2'-hydroxymethyl-ethyl)-1β-ethyl-1,2,3,4,6,7-hexahydro-indolo [2,3-a] quinolizinium-dibenzoyl tartarate are obtained. The base content of the product is 55.4% according to perchloric acid titration.

$[\alpha]^{20}_D = -72.3°$ (c = 1, dimethyl formamide)
Melting point: 140°–142° C. (decomposition)
Yield: 52.0%.

Then 40 ml of 5% sodium carbonate solution are added to the filtrate at a temperature of 20° C. to 25° C. and 100 ml of water are added. The precipitated substance is filtered off, washed with 5% acetonic water and dried.

Thus 3.42 g (7.52 millimoles) of (+)-14,14 bis-(ethoxycarbonyl)-1α-ethyl-1,2,3,4,6,7,12,12b-octahydro-indolo[2,3-a] tetrahydropyranyl[2,3-c] quinolizine are obtained.

Active ingredient content (on the basis of titration with perchloric acid): 99.7%.

$[\alpha]^{20}_D = +95.8°$ (c = 1, dichloromethane)
Melting point: 134°14 137° C. (decomposition)
Yield: 47.0%

EXAMPLE 7

Resolution of
(±)-14,14-bis(ethoxycarbonyl)-1-ethyl-1,2,3,4,6,7,12,12b-octahydro-indolo 2,3-a tetrahydropyranyl [2,3-c] quinolizine (compound of formula Ia)

To 18.2 g (40 millimoles) of racemic 14,14-bis(ethoxycarbonyl-1-ethyl-1,2,3,4,6,7,12,12b-octahydro-indolo [2,3-a] tetrahydropyranyl [2,3-c] quinolizine 180.0 ml of ethanol, 10.0 ml of dichloromethane and 15.0 g (40 millimoles) of (−)-dibenzoyl-d-tartaric acid monohydrate are added. Thus 17.4 g (21.4 millimoles) of (−)-1α-(2'-dicarbethoxy-2'-hydroxymethyl-ethyl)-1β-ethyl-1,2,3,4,6,7-hexahydro-indolo[2,3-a] quinolizinium-dibenzoyl tartarate are obtained. The base content of the product is 55.7% according to perchloric acid titration.

$[\alpha]^{20}_D = -7.25°$ (c = 1, dimethyl formamide)
Melting point: 139°–141° C. (decomposition)
Yield: 53.5%.

The filtrate is evaporated to half of its original volume by vacuum distillation. To the evaporation residue 100 ml of 5% sodium carbonate solution are added and 50 ml of water are added at a temperature of 20° to 25° C. The precipitated substance is washed with 5% ethanolic water and dried.

Thus 8.37 g (18.4 millimoles) of (+)-14,14-bis(ethoxycarbonyl)-1α-ethyl-1,2,3,4,6,7,12,12b-octahydro-indolo[2,3-a] tetrahydropyranyl[2,3-c] quinolizine are obtained.

Active ingredient content (on the basis of titration with perchloric acid): 99.8%. $[\alpha]^{20}_C = +95.8°$ (c=1, dichloromethane)
Melting point: 133°–136.5° C. (decomposition)
Yield: 46%.

EXAMPLE 8

Resolution of (±)-14,14-bis(methoxycarbonyl)-1-ethyl-1,2,3,4,6,7,12,12b-octahydro-indolo[2,3-a] tetrahydropyranyl [2,3-c] quinolizine (compound of formula Ia)

To 5.0 g (11.70 millimoles) of racemic 14,14-bis(methoxycarbonyl)-1-ethyl-1,2,3,4,6,7,12,12b-octahydro-indolo [2,3-a] tetrahydropyranyl 2,3-c quinolizine 35.0 ml of acetone and 3.08 g (8.2 millimoles) of (−)-dibenzoyl-d-tartaric acid are added. Then the reaction mixture is stirred at room temperature for 2 hours, the precipitated crystals are filtered off, washed with acetone and dried.

Thus 4.77 g (6.08 millimoles) of (−)-1α-(2′-dicarbmethoxy-2′-hydroxymethyl-ethyl)-1β-ethyl-1,2,3,4,6,7-hexahydro-indolo[2,3-a] quinolizinium-dibenzoyl tartarate are obtained. The base content of the product is 53.9% according to perchloric acid titration.

$[\alpha]^{20}_D = -73.2°$ (c=1, dimethyl formamide)
Melting point: 147°–149° C. (decomposition)
Yield: 52.0%.

Then 10 ml of 6% sodium carbonate solution are added to the filtrate at a temperature of 20° to 25° C., and 30 ml of water are slowly added. The precipitated substance is filtered off, washed with 5% acetonic water and dried.

Thus 2.35 g (5.5 millimoles) of (+)-14,14-bis(methoxycarbonyl)-1α-ethyl-1,2,3,4,6,7,12,12b-octahydroindolo[2,3-a] tetrahydropyranyl[2,3-c] quinolizine are obtained.

Active ingredient content (on the basis of titration with perchloric acid): 99.7%.
$[\alpha]^{20}_D = +101.5°$ (c=1, dichloromethane)
Melting point: 142°–150° C. (decomposition)
Yield: 47.0%.

EXAMPLE 9

Resolution of (±)-14,14-bis(methoxycarbonyl)-1-ethyl-1,2,3,4,6,7,12,12,b-octahydro-indolo [2,3-a] tetrahydropyranyl[2,3-c] quinolizine (compound of formula Ia)

To 17.2 g (40 millimoles) of (±)-14,14-bis(methoxycarbonyl)-1-ethyl-1,2,3,4,6,7,12,12b-octahydro-indolo [2,3-a] tetrahydropyranyl[2,3-c] quinolizine 150 ml of methanol and 15.1 g (40 millimoles) of (−)-dibenzoyl-d-tartaric acid are added. Then the reaction mixture is stirred for 2 hours at a temperature of 20° to 25° C., the precipitated product is filtered off, washed with methanol and dried.

Thus 16.48 g (21 millimoles) of (−)-1α-(2′-dicarbomethoxy-2′-hydroxymethyl-ethyl)-1β-ethyl-1,2,3,4,6,7-hexahydro-indolo [2,3-a] quinolizinium-dibenzoyl tartarate are obtained.

The base content of the product is 54.1% according to perchloric acid titration.

$[\alpha]^{20}_D = -73.5°$ (c=1, dimethyl formamide)
Melting point: 146°–149° C. (decomposition)
Yield 52.5%.

The filtrate is evaporated in vacuo, the evaporation residue is dissolved in 50 ml of dichloromethane and extracted with 80 ml of 5% sodium carbonate solution The filtrate is evaporated in vacuo, 20 ml of acetone are added to the evaporation residue at a temperature of 20° to 25° C., and 50 ml of water are slowly added under stirring. The precipitated substance is filtered off, washed with water and dried.

Thus 7.94 g (18.6 millimoles) of (+)-14,14-bis(methoxycarbonyl)-1α-ethyl-1,2,3,4,6,7,12,12b-octahydroindolo [2,3-a] tetrahydropyranyl [2,3-c] quinolizine are obtained.

Active ingredient content (on the basis of titration with perchloric acid): 99.6%.
$[\alpha]^{20}_D = +100.2°$ (c=1, dichloromethane)
Melting point: 144°–150° C. (decomposition)
Yield: 46.5%.

EXAMPLE 10

Resolution of (±)-14,14-bis(ethoxycarbonyl)1-ethyl-1,2,3,4,6,7,12,12,b-octahydro-indolo [2,3-a] tetrahydropyranyl [2,3-c] quinolizine (compound of formula Ia)

To 1.82 g (4 millimoles) of racemic 14,14-bis(ethoxycarbonyl)-1-ethyl-1,2,3,4,6,7,12,12b-octahydro-indolo [2,3-a] tetrahydropyranyl [2,3-c] quinolizine 18 ml of ethanol then 1.5 g (4 millimoles) of (+)-dibenzoyl-d-tartaric acid are added.

Thus 1.7 g of (+)-1-(2′-dicarbethoxy-2′-hydroxymethyl-ethyl)-1α-ethyl-1,2,3,4,6,7-hexahydro-indolo [2,3-a] quinolizinium-dibenzoyl-d-tartarate are obtained. The base content of the product is 55.0% according to perchloric acid titration. $[\alpha]^{20}_D = +72.6°$ (c=1, dimethyl formamide)
Melting point: 139°–141° C. (decomposition)
Yield: 53.5%.

The mother liquor is evaporated to half of its original volume in vacuo. To the residue 10 ml of 5% sodium carbonate solution are added at a temperature of 20° C.; then 5 ml of water are added. The precipitated substance is filtered, off, washed with 5% ethanolic water and dried.

Thus 0.82 g (45%) of (−)-14,14bis(ethoxycarbonyl)-1β-ethyl-1,2,3,4,6,7,12,12b-octahydro-indolo[2,3-a] tetrahydropyranyl[2,3-c] quinolizine are obtained.
$[\alpha]^{20}_D = -94°$ (c=1, dichloromethane)
Melting point: 134°–136° C. (decomposition)

EXAMPLE 11

Preparation of (−)-1β-(2′-diethoxycarbonyl-2′-hydroxymethyl-ethyl)-1α-ethyl-1,2,3,4,6,7,12,12,bα-octahydro-indolo[2,3-a] quinolizine 30.0 g (0.066 mole) of (+)-14,14-(ethoxycarbonyl)-1α-ethyl-1,2,3,4,6,7,12,12b-octahydro-indolo [2,3-a] tetrahydropyranyl [2,3-c] quinolizine are dissolved in 60 ml of dimethyl formamide, then hydrogenated in the presence of 0.3 g of 10% palladium-on-charcoal catalyst at a temperature of 40° C. under atmospheric pressure. The calculated amount of hydrogen is taken up by the mixture within about 2 hours; then the catalyst is filtered of 100 ml of water are added to the reaction mixture and the solution is extracted three times with 50 ml of chloroform.

The organic phase is washed with 2×40 ml of water, dried over sodium sulfate and evaporated to dryness in vacuo. The residue is taken up with 50 ml of ethanol and acidified to pH=4 with hydrochloric ethanol. The precipitated crystalline substance is filtered off and washed with ethanol. Thus 29.5 g (91%) of the desired compound are isolated.

Melting point: 214°–218° C.
$[\alpha]^{20}_D = -28.9°$ (c=1, dimethyl formamide)
IR (KBr): 3340 (OH, NH); 1730 (CO); 1240 (beta-OH); 1040 (C—OH) cm$^{-1}$
MS (M/e, %): 456 (M+:7); 426 (83); 411 (10); 397 (7); 381 (45); 353 (15); 307 (15); 267 (100); 197 (7); 184 (5); 169 (11).

EXAMPLE 12

Preparation of (−)-1β-(2′-ethoxycarbonyl-2′-hydroxyimino)-ethyl-1α-ethyl-1,2,3,4,6,7,12,12,a-octahydro-indolo [2,3-a] quinolizine hydrochloride To 4.56 g (10 millimoles) of (−)-1β-(2′-diethoxycarbonyl-2′-hydroxymethyl-ethyl)-1α-ethyl-1,2,3,4,6,7,12,12b-alpha-octahydro [2,3-a] quinolizine 30 ml of ethanol of 0.56 g of potassium hydroxide (10 millimoles) dissolved in 3 ml of water are added and the reaction mixture is stirred for 1 hour at a temperature of 20° to 25° C. Ethanol is distilled off under vacuo, then 20 ml of acetic acid and 1.38 g (20 millimoles) of sodium nitrite dissolved in 3 ml of water are added at a temperature of 10° to 15° C. The reaction mixture is kept at this temperature for 2 hours, then cooled below 10° C. and 12 ml of 18% hydrochloric acid are added and the product is precipitated. The substance thus obtained is filtered off, washed with water and dried. Thus 3.44 g (8.2 millimoles) of desired product are obtained.

Yield: 82%.
Melting point: 257°–260° C.
$[\alpha]^{20}_D = -62°$ (c=1, dimethyl formamide)

EXAMPLE 13

Preparation of (+)cis-apovincaminic acid ethylester 4.75 g (0.025 mole) of p-toluene sulfonic acid monohydrate are dried with toluene at reflux temperature under atmospheric pressure in a flask equipped with Marcusson distiller, then toluene is supplemented to 70 ml and 4.2 g (0.01 mole) of (−)-1β-[(2′-ethoxycarbonyl-2′-hydroxyimino)-ethyl]-1α-ethyl-1,2,3,4,6,7,12,12a-octahydro-indolo [2,3-a] quinolizine hydrochloride are added. The reaction mixture is refluxed for 1.5 hours, then cooled to room temperature and 30 ml of water are added. The pH of the mixture is set to 9 with aqueous ammonium hydroxide solution. After separation the toluene phase is dried, clarified with charcoal, filtered off and the filtrate is evaporated under vacuo until an oily substance is obtained. The evaporation residue is boiled with 5 ml of ethanol; the precipitated substance is filtered off at 0° C. and dried Thus 3.14 g of aimed product is obtained.

Yield 90%.
Melting point: 148°–151° C.
$[\alpha]^{20}_D = +147°$ (c=1, chloroform)

EXAMPLE 14

Preparation of (−)-eburnamonine (3α,16α)
Air is led through a mixture of 3.71 g (0.01 mole) of (−)-1α-ethyl-1β-(2′-methoxycarbonyl-2′-hydroxyimino-ethyl)-1,2,3,4,6,7,12,12,a-octahydro-indolo [2,3-a] quinolizine, 50 ml water and 2.0 g (0.05 mole) of solid sodium hydroxide at a temperature of 92° to 96° C. for 1 hour under stirring. Then the reaction mixture is cooled to room temperature and 7.4 g (0.075 mole) of 37% aqueous hydrochloric acid solution are added and the mixture is stirred for 1.5 hours at a temperature of 95° to 100° C. Thereafter the reaction mixture is cooled to room temperature, 30.0 ml of dichloromethane are added, then the pH of the mixture is adjusted to 9 by adding concentrated aqueous ammonium hydroxide solution. Then the phases are separated the aqueous phase is extracted with 2×5.0 ml of dichloromethane, the organic phases are unified, dried over solid anhydrous sodium sulfate then filtered off. The solvent of the filtrate is changed to 6.0 ml of methanol by atmospheric distillation. Then the reaction mixture is cooled to a temperature of 0° C., the precipitated substance is filtered off, washed with a small amount of cooled methanol and dried. Thus 2.83 g of desired product are obtained.

Yield: 96.5%.
Melting point: 176.5°–177.5° C.
$[\alpha]^{20}_D = -94.9°$ (c=1, chloroform). Substance content: 99.2% (according to HPLC analysis).

We claim:

1. A process for the preparation of a compound of the Formula (Ia)

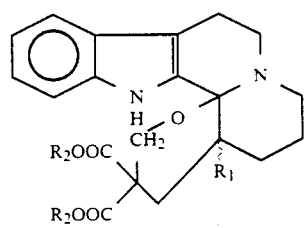

wherein
R$_1$ and R$_2$ are independently alkyl having 1 to 4 carbon atoms;
or a pharmaceutically acceptable acid addition salt thereof of the Formula (Ib)

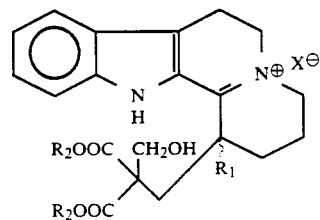

where X is an acid residue, which comprises reacting a compound of the Formula (II)

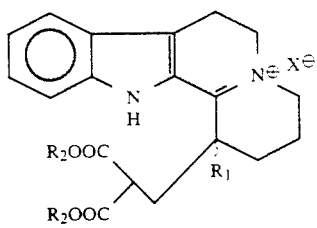

with formaldehyde in the presence of a base and, if desired, resolving the racemic compound of the Formula (Ia) thus obtained or transforming the same into a pharmaceutically acceptable acid addition salt of the Formula (Ib).

2. The process defined in claim 1 which comprises carrying out the reaction in an inert organic solvent or in an aqueous solvent mixture where for every mole of the compound of the Formula (II) there is employed a 10% to a 33% molar excess of the formaldehyde.

3. A compound of the Formula (Ia)

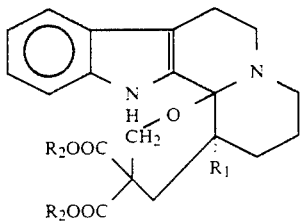

wherein
R₁ and R₂ are independently alkyl having 1 to 4 carbon atoms, or a pharmaceutically acceptable acid addition salt thereof of the Formula (Ib)

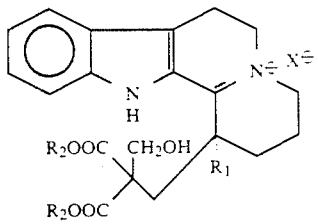

wherein
X is an acid residue.

4. (±)-1-ethyl-14,14-bis(ethoxycarbonyl)-2,3,4,6,7,12,12b-octahydro-indolo(2,3,-a)tetrahydropyranyl(2,3-c) quinolizine or a pharmaceutically acceptable acid addition salt thereof as defined in claim 3.

5. (±)-1-ethyl-14,14-bis(methoxycarbonyl)-1,2,3,4,6,7,12,12b-octahydro-indolo(2,3,-a)tetrahydropyranyl (2,3-c) quinolizine or a pharmaceutically acceptable acid addition salt thereof as defined in claim 3.

6. (−)-14,14-bis(ethoxycarbonyl1beta-ethyl-1,2,3,4,6,7,12,12b-octahydro-indolo(2,3-a)tetrahydropyranyl (2,3-c) quinolizine or a pharmaceutically acceptable acid addition salt thereof as defined in claim 3.

7. (+)-14,14-bis(ethoxycarbonyl)-1alpha-ethyl-1,2,3,4,6,7,12,12b-octahydro-indolo(2,3-a)tetrahydropyranyl (2,3-c)quinolizine or a pharmaceutically acceptable acid addition salt thereof as defined in claim 3.

8. (+)-14,14-bis(methoxycarbonyl)-1alpha-ethyl-1,2,3,4,6,7,12,12b-octahydro-indolo(2,3-a)tetrahydropyranyl (2,3-c)quinolizine or a pharmaceutically acceptable acid addition salt thereof as defined in claim 3.

9. (−)-14,14-bis(methoxycarbonyl)-1beta-ethyl-1,2,3,4,6,7,12,12b-octahydro-indolo(2,3-a)tetrahydropyranyl(2,3-c) quinolizine or a pharmaceutically acceptable acid addition salt thereof as defined in claim 3.

* * * * *